(12) United States Patent
Jimoh

(10) Patent No.: US 6,369,001 B1
(45) Date of Patent: Apr. 9, 2002

(54) MICROEMULSION COFORMULATION OF A GRAMINICIDE AND A WATER-SOLUBLE HERBICIDE

(75) Inventor: Ganiyu A. Jimoh, St. Louis, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/633,193

(22) Filed: Aug. 4, 2000

Related U.S. Application Data

(60) Provisional application No. 60/148,423, filed on Aug. 11, 1999.

(51) Int. Cl.$^7$ ................................................ A01N 25/22
(52) U.S. Cl. ........................ 504/118; 504/363; 504/128
(58) Field of Search ................................ 504/128, 363, 504/118

(56) References Cited

U.S. PATENT DOCUMENTS

| | | |
|---|---|---|
| 3,799,758 A | 3/1974 | Franz |
| 3,853,530 A | 12/1974 | Franz |
| 4,140,513 A | 2/1979 | Prill |
| 4,315,765 A | 2/1982 | Large |
| 4,405,531 A | 9/1983 | Franz |
| 4,481,026 A | 11/1984 | Prisbylla |
| 4,507,250 A | 3/1985 | Bakel |
| 5,750,468 A | 5/1998 | Wright et al. |

FOREIGN PATENT DOCUMENTS

| | | |
|---|---|---|
| EP | 0146238 | 6/1985 |
| GB | 2267825 A | 12/1993 |
| WO | WO97/31535 | 9/1997 |
| WO | WO98/09525 | 3/1998 |

OTHER PUBLICATIONS

Squires & Glatt, Research Report, Expert Committee for Weeds of Western Canda, 34(2), p. 527 (1987).
Farm Chemicals Handbook, Meister Publishing Co., 1999, lists at page C351.
The Pesticide Manual, 11th edition, published by British Crop Protection Council, 1997, p. 1089.

*Primary Examiner*—S. Mark Clardy
(74) *Attorney, Agent, or Firm*—Senniger, Powers, Leavitt & Roedel; Joseph A. Schaper

(57) ABSTRACT

A liquid concentrate herbicidal microemulsion composition is provided comprising (i) water;
(ii) a water-soluble herbicide;
(iii) an oil-soluble cyclohexenone or aryloxyphenoxypropionate graminicide in a weight ratio to the water-soluble herbicide of about 1:50 to about 1:1;
(iv) a substantially water-immiscible organic solvent selected such that the graminicide has an organic solvent/water partition coefficient, expressed as a logarithm, of about 4 or greater, in a weight ratio to the graminicide of about 3:1 to about 30:1;
(v) an emulsifying system comprising one or more surfactants each having a tertiary amine functional group, in an amount not exceeding about 10% by weight but sufficient to provide acceptable physical stability of the microemulsion;
(vi) zero to a stabilizing amount of one or more water-soluble chlorides selected from hydrochloric acid, alkali metal chlorides, ammonium chloride, low molecular weight organic ammonium chlorides and quaternary ammonium chloride surfactants; and
(vii) a dispersing system comprising one or more nonionic surfactants, in a total amount not exceeding about 5% by weight but sufficient to provide acceptable dispersion of the microemulsion upon dilution thereof in a suitable volume of water for application to plants and not sufficient to destabilize the microemulsion.

Compositions of the invention wherein the water-soluble herbicide is a salt of glyphosate are particularly useful for controlling unwanted glyphosate-tolerant plants of the grass family in glyphosate-tolerant broadleaf crops.

26 Claims, No Drawings

MICROEMULSION COFORMULATION OF A GRAMINICIDE AND A WATER-SOLUBLE HERBICIDE

CROSS-REFERENCE TO RELATED APPLICATIONS

This application claims the benefit of U.S. Provisional Application No. 60/148,423 filed Aug. 11, 1999.

FIELD OF THE INVENTION

The present invention relates to compositions useful in agriculture comprising at least two herbicidal active ingredients, one of which is a selective graminicide of the cyclohexenone class or the aryloxyphenoxypropionate class and the other of which is a water-soluble herbicide. In particular, the present invention relates to stable liquid concentrate compositions of such active ingredients.

BACKGROUND OF THE INVENTION

As a means of killing or otherwise controlling unwanted plants, especially weeds, in agriculture and related endeavors, it is desirable to treat such plants or the locus thereof with chemical herbicides. Commonly such treatment has to be done in presence of plants, especially crop plants, which it is desired not to injure to an unacceptable degree. For this reason selective herbicides, that is, compounds having useful herbicidal activity against certain species of weeds but acceptably non-injurious to the particular crop in which these weeds occur, have been developed for a wide range of agricultural applications. In addition, certain crop plants have been developed by conventional breeding methods and by methods involving genetic transformation to tolerate certain herbicides that would otherwise injure or kill them.

A common problem with a selective herbicide is that its weed control spectrum, that is, the range of weed species effectively controlled by the herbicide, does not embrace the full diversity of weeds present in a crop. It has therefore been common to apply two or more herbicides simultaneously in order to achieve the desired spectrum of control. Two or more different herbicides, separately packaged as concentrate formulations, can be admixed with water in a spray tank by the end user, a method known as tank-mixing. More conveniently, however, the different herbicides can be coformulated in a single concentrate formulation, requiring only dilution in water by the end user prior to application by spraying. Such a formulation is often known as a package-mix.

Package-mix formulations present numerous challenges to the formulator of agricultural chemicals such as herbicides. For example, the formulation should contain the herbicidal active ingredients at as high a total concentration as possible, for maximum convenience to the end user and to minimize packaging and shipping costs, while keeping the active ingredients in the desired weight ratio one to the other. Most importantly, the package-mix formulation must exhibit sufficient physical and chemical stability to have an effective shelf life of at least a few months, preferably at least a year, ideally at least two years.

Where the package-mix formulation contains a first herbicide that is oil-soluble and that undergoes chemical degradation, even at a slow rate, in water, and a second herbicide that is water-soluble, the challenge of providing a storage-stable liquid concentrate formulation is particularly acute. Water used as the solvent for the second herbicide acts as a degradation medium for the first herbicide. Hydrolysis is the most common water-mediated degradation mechanism.

Graminicides are selective herbicides having strong herbicidal activity against many grass species but generally relatively non-phytotoxic to dicotyledonous species, including dicotyledonous crops such as cotton, rapeseed (including canola), soybeans and sugar beet. There are two main classes of selective graminicides in widespread use in agriculture: cyclohexenones, sometimes called "dims", and aryloxyphenoxypropionates, sometimes called "fops". Among commercially significant oil-soluble "dims" are butroxydim, clethodim, cycloxydim, sethoxydim, tepraloxydim and tralkoxydim. Among commercially significant "fops" are clodinafop-propargyl, cyhalofop-butyl, diclofop-methyl, fluazifop-butyl, fluazifop-P-butyl, haloxyfop, propaquizafop, quizalofop and quizalofop-P.

Because the spectrum of herbicidal activity of "dims" and "fops" is largely restricted to grasses, there is often great complementarity in a package-mix of a "dim" or "fop" with a second herbicide that has strong broadleaf herbicidal activity. Many such herbicides are most conveniently formulated as water-soluble salts in aqueous solution. Examples are salts of clopyralid, 2,4-D, dicamba, imazethapyr, MCPA and triclopyr.

Another situation where a "dim" or "fop" is a useful component of a package-mix is where the second herbicide has broad-spectrum or essentially non-selective herbicidal activity and where gramineous crops such as wheat, maize or rice have been bred to tolerate high doses of that herbicide. "Volunteer" plants of such herbicide-tolerant gramineous crops can become troublesome weeds in a succeeding broadleaf crop that is tolerant of the same herbicide. For example, in a crop rotation where glyphosate-tolerant soybeans follow glyphosate-tolerant corn (maize), "volunteer" corn cannot be controlled by glyphosate alone in the soybean crop. There is therefore advantage in adding a "dim" or "fop" to the glyphosate to ensure control of "volunteer" corn along with all the other weed species. Glyphosate is most conveniently formulated as a water-soluble salt in aqueous solution; the same is true of several other broad-spectrum herbicides including glufosinate.

Thus among the most desirable package-mix partner herbicides for a "dim" or "fop" are a number of water-soluble herbicides. It is often possible to formulate the package-mix as a dry particulate, for example granular, product; however for many purposes in agriculture a liquid concentrate formulation is preferred. Where the partner herbicide is water-soluble, as in the case of the salts mentioned above, such a liquid concentrate is preferably water-based.

A major problem is that most "dims" and "fops" exhibit some degree of chemical instability, primarily in the form of hydrolysis, in an aqueous medium; in the majority of cases this instability is pH-dependent. For example, tralkoxydim is especially unstable in an acid medium, whereas diclofop-methyl undergoes hydrolysis more readily in an alkaline medium.

It would therefore be a major advance in the art to provide a water-based liquid concentrate composition comprising a first herbicide that is a graminicide that degrades in an aqueous medium, and a second herbicide that is water-soluble, yet wherein the graminicide has acceptable long-term chemical stability.

As examples of a graminicide and a water-soluble herbicide, consider quizalofop-P and a salt of glyphosate respectively.

Quizalofop is a racemic mixture of R- and S-isomers of 2-[4-[(6-chloro-2-quinoxalinyl)oxy]phenoxy]propanoic acid and is most commonly used in the form of the ethyl ester (quizalofop-ethyl). Quizalofop-P is the R-isomer and is available in several ester forms of which the most widely used is the ethyl ester (quizalofop-P-ethyl). In water, quizalofop-P-ethyl exhibits hydrolytic instability, hydrolysis occurring most rapidly when pH is in the alkaline range.

Glyphosate (N-phosphonomethylglycine) in its strict sense is an acid compound, but the word "glyphosate" is herein used in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of the salts disclosed, the counterion to glyphosate anion is a relatively low molecular weight, non-amphiphilic cation. Typical of such salts are alkali metal, for example sodium and potassium, salts; ammonium salt; and salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup® brand, Accord® brand, Roundup® Ultra brand and Roundup® Xtra brand herbicides of Monsanto Company, which contain the isopropylammonium salt, Roundup® Dry brand and Rival® brand herbicides of Monsanto Company, which contain the ammonium salt, Roundup® Geoforce brand herbicide of Monsanto Company, which contains the sodium salt, and Touchdown® brand herbicide of Zeneca, which contains the trimethylsulfonium salt.

Squires & Glatt, *Research Report, Expert Committee for Weeds of Western Canada,* 34(2), page 527 (1987) reported evaluation of various herbicide treatments for weed control in fallow. Among the products said to be tested was a "commercial mix" of sethoxydim and the water-soluble herbicide 2,4-D amine salt, at a 1:5 weight ratio. It is believed that this refers to a commercial "co-pack", i.e., two separate formulations packaged in separate containers but sold together. *Farm Chemicals Handbook* '99 (Meister Publishing Co., 1999) lists at page C 351 a number of co-packs of sethoxydim with other herbicides. Use of co-packs, though less convenient for the end user than a single package-mix formulation, is common where it is difficult to provide a stable package-mix.

International Patent Application WO 98/09525 discloses that undesired plants can be controlled in crops resistant to phospho-herbicides, for example glufosinate or glyphosate, by treatment with a composition comprising a phospho-herbicide and a second herbicide, exemplified inter alia by the aryloxyphenoxypropionate graminicides propaquizafop and clodinafop. Numerous types of concentrate composition comprising the phospho-herbicide and the second herbicide are proposed therein. The only type that is water-based is a suspension concentrate, said to be prepared by intimately mixing 3–50% by weight of a finely ground active ingredient mixture with ethylene glycol, surfactants, small amounts of other excipient ingredients and water. The problem of chemical instability of the propaquizafop or clodinafop in such an aqueous formulation system is not addressed.

International Patent Application WO 97/31535 discloses combinations of an alkyl ester of glyphosate with a second herbicide that can be, for example, clethodim, clodinafop-propargyl, cycloxydim, cyhalofop-butyl, diclofop-methyl, fluazifop-butyl, haloxyfop-ethoxyethyl, propaquizafop, quizalofop-ethyl, quizalofop-P-tetrahydrofurfuryl, sethoxydim or tralkoxydim. No suggestion is made of a water-based concentrate composition comprising these ingredients.

European Patent Application No. 0 146 238 discloses a herbicidal composition comprising glyphosate or a salt thereof and an aryloxyphenoxypentanoate herbicide.

Liquid concentrate coformulations of two active ingredients, one water-soluble and the other oil-soluble, are known in the art in the form of emulsions, most commonly of the oil-in-water type having a discontinuous oil phase dispersed in a continuous aqueous phase with the aid of one or more emulsifying agents. The water-soluble active ingredient is contained predominantly in the aqueous phase and the oil-soluble active ingredient predominantly in the oil phase. The individual oil particles can be large enough to interfere with the transmission of light, giving rise to a cloudy or milky emulsion known as a macroemulsion. However, where the individual oil particles are so small as to allow light to be transmitted without noticeable scattering, the emulsion is clear, i.e., transparent, and is known as a microemulsion.

Microemulsions offer a number of practical advantages, one of the most important being that they typically remain homogeneous without agitation for long periods of time. In this respect, to the agricultural technician or other user, a microemulsion formulation can be handled with the same ease and convenience as a simple aqueous solution. However, selection of excipient ingredients for preparation of a microemulsion is not straightforward or easy.

The difficulty of preparing a stable microemulsion is compounded when the active ingredients to be coformulated are a water-soluble herbicide and an oil-soluble gramninicide, and the resulting product has to meet the requirements of the end user for effective weed control and, where the product is to be applied in a crop, good crop safety. Such a combination of active ingredients presents a number of challenges.

One challenge is that water-mediated chemical degradation, e.g., hydrolysis, of the graminicide must be minimized. This is an especially difficult challenge in a microemulsion, where the oil particles containing the graminicide are extremely small and therefore present a very large interfacial area with the aqueous phase.

Another challenge is that surfactants must be present for a number of reasons: (a) as emulsifying agents to physically stabilize the microemulsion, (b) as dispersants to prevent aggregation of oil particles when the microemulsion is diluted in water for application to plants, and (c) as adjuvants to enhance herbicidal efficacy of one or both active ingredients, for example by improving retention on or adhesion to foliar surfaces of the applied composition or by improving penetration of the active ingredient(s) through the cuticle to the interior of plant foliage. Surfactants tend to facilitate transfer of the graminicide across the large interface between oil and aqueous phases, increasing the potential for chemical degradation.

These and other challenges have now surprisingly been met by an invention set out immediately below.

SUMMARY OF THE INVENTION

The present invention provides a liquid concentrate herbicidal composition that is a microemulsion comprising a continuous aqueous phase having a discontinuous oil phase dispersed therein. The aqueous phase comprises water wherein is dissolved a water-soluble herbicide. The oil phase comprises a substantially water-immiscible organic solvent wherein is dissolved an oil-soluble graminicide having the chemical formula (I)

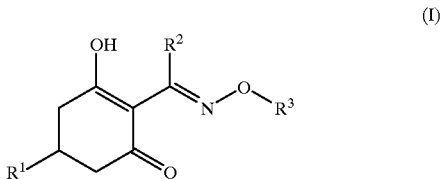

(I)

where $R^1$ is a butyryl, (2-ethylthio)propyl or 2,4,6-trimethylphenyl group or a group

wherein X is O or S; $R^2$ is a $C_{1-4}$ alkyl group; and $R^3$ is an ethyl, allyl or 3-haloallyl group; or the chemical formula (II)

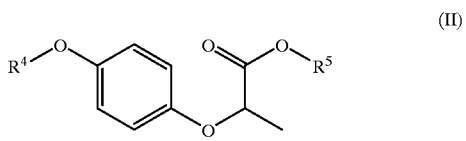

(II)

where $R^4$ is a group

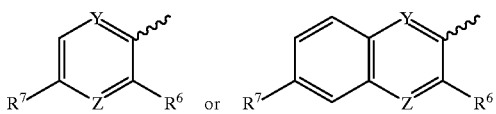

wherein $R^6$ and $R^7$ are independently selected from hydrogen, halogen, methyl, trifluoromethyl and cyano groups, and Y and Z are independently selected from CH and N, at least one of Y and Z being N; and $R^5$ is a hydrogen, $C_{1-4}$ alkyl, allyl, propargyl, tetrahydrofurfuryl, 2-ethoxyethyl or 2-isopropylideneaminooxyethyl group. The water-soluble herbicide is present in an amount which is biologically effective when the composition is diluted in a suitable volume of water and applied to foliage of a susceptible plant, and the oil-soluble graminicide is present in a weight ratio to the water-soluble herbicide of about 1:50 to about 1:1.

The organic solvent is (a) selected such that the graminicide has an organic solvent/water partition coefficient, expressed as a logarithm, of about 4 or greater and (b) included in an amount such that the weight ratio of the organic solvent to the graminicide is about 3:1 to about 30:1.

The composition further comprises (a) an emulsifying system comprising one or more surfactants each having a tertiary amine functional group, in an amount not exceeding about 10% by weight but sufficient to provide acceptable physical stability of the microemulsion, (b) zero to a stabilizing amount of one or more water-soluble chlorides selected from hydrochloric acid, alkali metal chlorides, ammonium chloride, low molecular weight organic ammonium chlorides and quaternary ammonium chloride surfactants, and (c) a dispersing system comprising one or more nonionic surfactants, in a total amount not exceeding about 5% by weight but sufficient to provide acceptable dispersion of the microemulsion upon dilution thereof in a suitable volume of water for application to plants and not sufficient to destabilize the microemulsion.

An amount of the selected emulsifying system "sufficient to provide acceptable physical stability of the microemulsion" can be readily determined by one of skill in the art by routine evaluation of a range of compositions having differing amounts of the emulsifying system. Physical stability of the microemulsion is acceptable if no significant phase separation is evident following storage for at least 7 days at any temperature in the range from about 0° C. to about 40° C. Where the microemulsion is one that additionally requires the presence of a water-soluble chloride for acceptable physical stability, routine evaluation of differing amounts of the emulsifying system is conducted in presence of such water-soluble chloride.

A "stabilizing" amount of one or more selected water-soluble chlorides is an amount that provides acceptable physical stability of the microemulsion as defined immediately above, when present along with an emulsifying system in an amount insufficient on its own to provide such stability. One of skill in the art can readily determine such a stabilizing amount by routine evaluation of a range of compositions having differing amounts of the selected chloride(s).

An amount of the selected dispersing system "sufficient to provide acceptable dispersion of the microemulsion upon dilution thereof in a suitable volume of water for application to plants" can readily be determined by one of skill in the art by routine evaluation of a range of compositions having differing amounts of the selected dispersing system. A suitable volume of water is that which upon dilution of the microemulsion provides an application composition having a concentration of active ingredients adequate to kill or control susceptible plants if applied to foliage of such plants. Dispersion of the microemulsion in such a volume of water is acceptable if no visible aggregation or flocculation of water-insoluble ingredients is observed.

An amount of the selected dispersing system "not sufficient to destabilize the microemulsion" is an amount lower than that which results in the microemulsion losing the acceptable physical stability it has in the absence of the dispersing system. Such an amount can readily be determined by one of skill in the art by routine evaluation of a range of compositions having differing amounts of the selected dispersing system.

DETAILED DESCRIPTION OF THE INVENTION

A liquid composition of the invention is an oil-in-water microemulsion. A water-soluble herbicide is present in solution in the continuous aqueous phase of the microemulsion, and an oil-soluble herbicide, more specifically an oil-soluble cyclohexenone or aryloxyphenoxypropionate graminicide, is present in solution in the discontinuous oil phase of the microemulsion. The composition is a herbicidal concentrate, i.e., it is normally diluted in a suitable volume of water before application, for example by spraying on to foliage of plants. Typically a concentrate composition contains at least about 5% by weight, and can contain up to about 50% by weight, of active ingredients, in the present case at least about 5% and up to about 50% by weight in total of the water-soluble herbicide and the oil-soluble graminicide. Preferably a composition of the invention contains at least about 10% by weight, more preferably at least about 20% by weight, in total of the water-soluble herbicide and the oil-soluble graminicide.

As indicated above, the oil-soluble graminicide is present in a weight ratio to the water-soluble herbicide of about 1:50 to about 1:1. Thus the concentration of the graminicide in the composition as a whole is about 0.1% to about 25% by weight. In preferred compositions the concentration of the graminicide is about 0.5% to about 10%, for example about 1% to about 5%, by weight.

In preferred compositions, the graminicide is selected from butroxydim, clethodim, cycloxydim, sethoxydim, tepraloxydim, tralkoxydim, haloxyfop, propaquizafop and the $C_{1-4}$ alkyl and propargyl esters of clodinafop, cyhalofop, diclofop, fluazifop, fluazifop-P, quizalofop and quizalofop-P. Where the water-soluble herbicide is a salt of glyphosate, an especially preferred graminicide is quizalofop-ethyl or quizalofop-P-ethyl.

A key to the present invention is to select as the solvent for the graminicide, i.e., as the basis for the oil phase, an organic liquid having the following properties. First, the solvent must be immiscible with water. Second, the affinity of the solvent for the graminicide in question must be such that substantially all of the graminicide is partitioned in the oil phase and substantially none in the aqueous phase. One of skill in the art will readily be able to determine whether a particular organic solvent meets this second criterion for the graminicide in question by following any standard test procedure for determining partition of a compound (in this case, the graminicide) between water and the organic solvent.

One such test procedure comprises the following steps.
1. A solution of the graminicide is prepared in the organic solvent at as high a concentration as possible up to 15% by weight.
2. An aliquot of 10 g of this solution is added to 90 g water in a glass bottle, which is shaken on a mechanical shaker for 4 h at ambient temperature.
3. The contents of the glass bottle are permitted to phase separate for 4 days.
4. Subsamples of the resulting oil and water phases are taken and analyzed by HPLC to determine concentrations $C_O$ and $C_W$ in the oil and water phases respectively. The subsample of the water phase is preferably centrifuged before analysis to remove traces of organic solvent.
5. A partition coefficient, analogous to octanol-water partition coefficient P, is calculated as $C_O/C_W$. The partition coefficient is conveniently expressed as a logarithm.

In many cases the concentration of the graminicide in the water phase will be below the detection limit of the HPLC method. In other cases traces of the organic solvent are found in the water phase, even after centrifugation, so that the apparent concentration of graminicide observed in the water phase is misleadingly high. In such cases, a published value for solubility in water of the graminicide in question can be used in place of $C_W$ for calculation of partition coefficient.

The organic solvent is selected such that the graminicide exhibits a partition coefficient such that $\log(C_O/C_W)$ is about 4 or greater, preferably about 5 or greater. Preferably the graminicide is soluble in the organic solvent at least at about 5% by weight, more preferably at least at about 10% by weight and most preferably at least at about 15% by weight. The higher the solubility of the graminicide therein, in general the more suitable is the organic solvent, provided such solvent is not miscible with water.

Organic solvents useful in compositions of the present invention preferably have a flash point above about 35° C., more preferably above about 90° C., and are preferably not antagonistic to the herbicidal effectiveness of either of the herbicides. Examples of suitable solvents include Solvesso™ Aromatic 100, Aromatic 150 and Aromatic 200, which are alkyl naphthalenic aromatic solvents available from Exxon, and Exxate™ 1000, an alkyl acetate with high solvency, also available from Exxon. Especially where the water-soluble herbicide is a salt of glyphosate, an aromatic solvent is particularly preferred.

Illustratively, 10 g of a 15% by weight solution of quizalofop-P-ethyl in Solvesso™ Aromatic 150 is added to 90 g water. The procedure described above for determination of partition coefficient is followed. The concentration $C_O$ of quizalofop-P-ethyl in the oil phase is found to be 14.81% by weight. The concentration $C_W$ of quizalofop-P-ethyl in the water phase is found to be 0.00017% by weight. $\log(C_O/C_W)$ is calculated as 4.94. However, $C_W$ in this case is significantly greater than the published solubility of quizalofop-P-ethyl in water (0.4 mg/l, or about 0.00004%; see *The Pesticide Manual,* 11th edition, published by British Crop Protection Council, 1997, p. 1089). If a true value of $C_W$ is set at 0.00004%, and the true concentration $C_O$ in the oil phase is effectively 15%, a theoretical $\log(C_O/C_W)$ can be calculated as 5.57.

The amount of the selected organic solvent to be used is important. Clearly the amount must be sufficient to completely dissolve the graminicide. Even for an organic solvent in which the graminicide is highly soluble, the weight ratio of organic solvent to graminicide should not be less than about 3:1. If too small an amount of organic solvent is used, protection of the graminicide from water can be compromised, leading to increased rates of chemical degradation. The weight ratio of organic solvent to graminicide can be much higher than 3:1, but economics and environmental considerations typically militate against excessively high amounts of organic solvent. Thus an upper limit of the weight ratio for practical purposes is about 30:1. Preferably the weight ratio of organic solvent to graminicide is about 3:1 to about 15:1, more preferably about 4:1 to about 10:1.

The aqueous phase of a composition of the invention comprises water having dissolved therein the selected water-soluble herbicide. The term "water-soluble" as used herein in relation to a herbicide or salt thereof means having a solubility in deionized water at 20° C. of not less than about 50 g/l. Preferred water-soluble herbicides have a solubility in deionized water at 20° C. of not less than about 200 g/l. Particularly preferred water-soluble herbicides have a herbicidally active acid or anionic moiety and are most usefully present in a composition of the invention in the form of one or more water-soluble salts. The aqueous phase can optionally contain, in addition to the water-soluble herbicide, other salts contributing to the ionic strength of the aqueous phase.

A particularly preferred group of water-soluble herbicides are those that are normally applied post-emergence to the foliage of plants. While the invention is not limited to any particular class of foliar-applied water-soluble herbicide, it has been found to provide useful benefits for compounds that rely at least in part for their herbicidal effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected symplastically by plasmodesmata, or via both apoplastic and symplastic pathways. For foliar-applied systemic herbicides, the most important pathway is the phloem, and the present invention is believed to provide the greatest benefits where the water-soluble herbicide is phloem-mobile. However, compositions of the invention can also be useful where the water-soluble herbicide is non-systemic, as in the case of paraquat.

Illustratively water-soluble herbicides that can be used in compositions of the invention include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

Phloem-mobile herbicides that are preferred for use in compositions of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr. A particularly preferred group of water-soluble herbicides are salts of bialaphos, glufosinate and glyphosate. Another particularly preferred group of water-soluble herbicides are salts of imidazolinone herbicides.

Compositions of the invention can optionally contain more than one water-soluble herbicide in solution in the aqueous phase.

An especially preferred herbicide useful in a composition of the present invention is glyphosate, the acid form of which is alternatively known as N-phosphonomethylglycine. Illustratively, glyphosate salts useful herein are disclosed in U.S. Pat. Nos.3,799,758 and 4,405,531. Glyphosate salts that can be used according to the present invention include but are not restricted to alkali metal, for example sodium and potassium, salts; ammonium salt; $C_{1-6}$ alkylammonium, for example dimethylammonium and isopropylammonium, salts; $C_{1-6}$ alkanolammonium, for example monoethanolammonium, salt; $C_{1-6}$ alkylsulfonium, for example trimethylsulfonium, salts; and mixtures thereof. The N-phosphonomethylglycine molecule has three acid sites having different pKa values; accordingly mono-, di- and tribasic salts, or any mixture thereof, or salts of any intermediate level of neutralization, can be used.

Contemplated compositions of the invention comprising a salt of glyphosate and an oil-soluble graminicide typically contain about 50 to about 500 grams per liter of glyphosate, expressed as acid equivalent (g a.e./l). Higher glyphosate concentrations within this range, for example about 300 to about 500 g a.e./l, are preferred.

A composition of the invention further comprises one or more surfactants. As indicated above, these surfactants can function as emulsifying agents, dispersing agents and/or adjuvants for herbicidal efficacy enhancement. However, the presence of surfactants can be detrimental as they can facilitate contact of the graminicide with water, thereby promoting chemical degradation of the graminicide.

An important feature of the invention is the discovery that, when an emulsifying system and dispersing system are selected in accordance with the invention, chemical degradation can be kept to an acceptable minimum by including less than about 10% by weight of the emulsifying system and less than about 5% of the dispersing system in the composition. Preferably the amount of all surfactants in the composition is less than about 12% by weight. Ideally the amount of surfactants included is not substantially more than the minimum needed for acceptable microemulsion physical stability and acceptable dispersibility in water. Minimum levels of emulsifying and dispersing systems can readily be determined by one of skill in the art as indicated above.

The emulsifying system in a composition of the invention comprises one or more surfactants each having a tertiary amine function. Such surfactants have a hydrophobic moiety comprising a linear or branched saturated or unsaturated aliphatic hydrocarbyl group having about 8 to about 22 carbon atoms, this moiety being referred to herein as an "alkyl" group consistent with conventional use of the term "alkyl" in surfactant-related literature.

Selection of such tertiary amine surfactants as the basis for the emulsifying system has the advantage that these surfactants typically also enhance the herbicidal effectiveness of the composition by various means, including assisting adherence to, and thereby retention on, plant foliage of the spray composition obtained by dilution in water of the present composition, and facilitating penetration of the active ingredients through the cuticle that covers the surface of plant foliage. This is especially true where the water-soluble herbicide is a salt of glyphosate. Quaternary ammonium surfactants can also be effective emulsifiers and provide good herbicidal efficacy enhancement; however these are not preferred in compositions of the invention because, at least when present in large amounts, they promote increased rates of chemical degradation of the graminicide. Without being bound by theory, it is believed that the increased chemical degradation associated with presence of quaternary ammonium surfactants results from the effectiveness of these surfactants in facilitating transfer of the graminicide from the oil phase to the aqueous phase. Highly water-soluble quaternary ammonium surfactants such as benzalkonium chloride (a mixture of alkyl dimethyl benzyl ammonium chlorides) are less troublesome in this regard than quaternary ammonium surfactants that are other than water-soluble, such as polyoxyethylene (2) N-methyl alkylammonium chlorides (N,N-bis(hydroxyethyl) N-methyl alkylammonium chlorides). Compositions of the invention preferably contain no substantial amount of quaternary ammonium surfactants that are other than water-soluble.

Tertiary amine surfactants for the emulsifying system are preferably selected from polyoxyethylene (2-20) tertiary alkylamines and polyoxyethylene (2-20) tertiary alkyletheramines. In particularly preferred examples the alkyl chains of these surfactants have about 12 to about 18 carbon atoms. Often the alkyl chains are derived from natural oils or fats such as coconut oil, soybean oil or beef tallow, and the resulting surfactants therefore typically contain a variety of alkyl chain lengths and degrees of unsaturation. Illustrative tertiary alkylamines include polyoxyethylene (2-10) cocoamine and polyoxyethylene (2-10) tallowamine, each available from many surfactant suppliers. Illustrative polyoxyethylene alkyletheramines are disclosed in U.S. Pat. No. 5,750,468 to Wright et al. It will often be found desirable to include at least two tertiary amine surfactants, one being more hydrophilic than the other, for example polyoxyethylene (5) tallowamine and polyoxyethylene (2) cocoamine respectively.

The minimum amount of tertiary amine surfactant(s) required to provide acceptable microemulsion stability depends, among other things, on the amount of organic solvent present, which depends in turn on the amount of graminicide present. In compositions of the invention the amount of tertiary amine surfactant(s) typically ranges from about 3% to about 10% by weight. Preferred compositions contain about 3% to about 8%, especially preferred compositions about 3% to about 6%, by weight in total of one or more tertiary amine surfactants.

For some graminicides, in particular for esters of quizalofop and quizalofop-P, it has been found that quaternary alkylammonium chloride surfactants are more effective emulsifying agents than the corresponding tertiary alkylamines. For example, polyoxyethylene (2-5) N-methyl alkylammonium chlorides are very effective emulsifiers. However, as indicated above, these quaternary ammonium surfactants are unacceptable because they promote chemical degradation of the graminicide. Yet, when tertiary amines alone are used, acceptable physical stability is not always achievable.

A solution to this problem lies in the surprising discovery that inclusion of water-soluble chlorides in the aqueous phase can provide enhanced microemulsion physical stability when tertiary amine surfactants are used as emulsifiers. Highly water-soluble quaternary ammonium chloride surfactants such as benzalkonium chloride are examples of such chlorides. These have a lesser tendency to promote graminicide chemical degradation than less water-soluble quaternary ammonium chlorides such as polyoxyethylene (2-5) N-methyl alkylammonium chlorides and they are therefore acceptable ingredients of compositions of the invention. However, it is nonetheless preferred that the amount of such water-soluble quaternary ammonium chloride surfactants does not exceed about 6% by weight of the composition. A minimum effective stabilizing amount of a water-soluble quaternary ammonium chloride surfactant can be determined by routine evaluation of physical stability in any particular situation. Where used, typical amounts of such a surfactant, for example benzalkonium chloride, are about 1% to about 6%, more preferably about 1% to about 4%, by weight of the composition.

Even more surprisingly, the desired enhancement of physical stability can be obtained by inclusion in the aqueous phase of a chloride that is not a surfactant. Low molecular weight ($C_{1-6}$) organic ammonium chlorides, for example isopropylammonium chloride, can be used, as can ammonium chloride or alkali metal chlorides such as sodium chloride or potassium chloride. Hydrochloric acid is also effective. Where the water-soluble herbicide is a salt of glyphosate, preferred water-soluble chlorides are ammonium chloride and hydrochloric acid. Hydrochloric acid can be especially useful where a downward adjustment of the pH of the aqueous phase is desired. An effective stabilizing amount of a water-soluble chloride in any particular situation can be determined by routine evaluation of physical stability as indicated previously. Where used, typical amounts of low molecular weight organic ammonium chlorides, ammonium chloride, alkali metal chlorides and/or hydrochloric acid are those providing about 0.5% to about 2.5% chloride ion by weight of the composition.

Any nonionic surfactant known to be effective as a dispersant for emulsion formulations can be used in the dispersing system of a composition of the invention. However, the dispersing system preferably comprises one or more nonionic surfactants selected from polyoxyethylene (2-20) alkylethers and alkylphenylethers, the term "alkyl" having the same meaning as in the context of the tertiary amine surfactants described above.

The amount of nonionic surfactant(s) forming the dispersing system of a composition of the invention is typically about 1% to about 5% by weight, preferably about 1% to about 3% by weight, of the composition. It has been found that if the amount of nonionic surfactant is too low, localized crop injury can sometimes occur. Without being bound by theory, it is believed that such localized injury results from inadequate dispersion of the oil phase, leading to locally high concentrations of organic solvent and graminicide at particular points on the foliar surface of the crop.

Compositions of the invention can optionally contain additional desired agriculturally acceptable ingredients, including surfactants of classes other than those defined above. Standard reference sources from which one of skill in the art can select suitable surfactants, without limitation to the above mentioned classes, include *Handbook of Industrial Surfactants,* Second Edition (1997) published by Gower, *McCutcheon's Emulsifiers and Detergents,* North American and International Editions (1997) published by MC Publishing Company, and *International Cosmetic Ingredient Dictionary,* Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

In a particularly preferred embodiment of the invention, the pH of the aqueous phase of the composition is in a range that is minimally conducive to chemical degradation of the oil-soluble graminicide. The water-soluble herbicide can, in some cases, naturally provide a pH in the desired range; in other cases an acid, e.g., hydrochloric acid, or base, e.g., potassium hydroxide or isopropylamine, can be added to adjust the pH. The effect of pH on degradation of the particular graminicide of choice can be determined by empirical testing, but is often known and available in standard reference sources such as *The Pesticide Manual,* 11th Edition (1997), published by the British Crop Protection Council. For example, quizalofop-P-ethyl exhibits greater chemical stability in acid to neutral than in alkaline media, whereas tralkoxydim is much more stable at pH 9 than at pH 5.

When an organic solvent is selected for the oil-soluble graminicide in accordance with the present invention, partition of the graminicide is so overwhelmingly in the oil phase that mean residence time in the aqueous phase of individual molecules of the graminicide is extremely short, and the opportunity for chemical degradation of the graminicide is accordingly very small. However, the adjustment of pH as just described is desirable to further reduce the potential for chemical degradation and permit the longest possible shelf-life for the composition.

A composition of the invention can optionally contain one or more additional herbicides each of which is other than water-soluble and other than a graminicide of the cyclohexenone or aryloxyphenoxypropionate classes. Such additional herbicides can be illustratively selected from acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clomazone, clomeprop, cloransulam-methyl, cyanazine, cycloate, cyclosulfamuron, daimuron, desmedipham, desmetryn, dichlobenil, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, rimsulfuron, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, triallate, triasulfuron, tribenuron, trietazine, trifluralin, triflusulfuron and vernolate.

A process of preparing a composition of the invention comprises mixing the various ingredients in a suitable vessel. A presently preferred order of addition of the ingredients is as follows. First, all required surfactants are added to a concentrated aqueous solution of the water-soluble herbicide, if desired along with an acid or base for pH adjustment, to form a first mixture. The oil-soluble graminicide is added to the organic solvent with agitation to form a second mixture. The second mixture is then added to the first mixture with agitation to form the finished composition.

An alternative order of addition is as follows. A concentrated aqueous solution of the water-soluble herbicide is prepared, together with other, optional, water-soluble ingredients including an acid or base for pH adjustment, with agitation to form a first mixture. The graminicide is added to the organic solvent with agitation to form a second mixture. The second mixture is added to the first mixture with agitation, then the surfactants are added. Agitation is continued until a physically stable microemulsion composition is formed.

Processes involving orders of addition other than those outlined above are also possible; some such processes are illustrated in the Examples herein.

The selection of application rates for a composition of the invention containing a specific water-soluble herbicide and specific graminicide in order to provide a desired level of herbicidal activity is within the skill of the ordinary agricultural technician. One of skill in the art will recognize that individual plant conditions, weather and growing conditions, as well as the specific exogenous chemical substance selected, can affect the results achieved in using a composition of the present invention. Where the water-soluble herbicide is a glyphosate salt, much information is available in published literature about appropriate application rates. Over two decades of glyphosate use and published studies relating to such use have provided abundant information from which a weed control practitioner can select glyphosate application rates that are herbicidally effective on particular species at particular growth stages in particular environmental conditions. Generally, preferred application rates for glyphosate are from about 100 to about 2500 g a.e./ha, more preferably from about 250 to about 1500 g a.e./ha.

The method of the present invention where the water-soluble herbicide is glyphosate, more particularly a water-soluble glyphosate salt, is applicable to any and all plant species on which glyphosate is biologically effective as a herbicide. This encompasses a very wide variety of plant species worldwide. Likewise, compositions of the invention containing a glyphosate salt can be applied to any and all plant species on which glyphosate is biologically effective.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp:), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, glyphosate/graminicide compositions of the present invention, and a process for treating plants with such compositions, can be useful on any of the above species. In a particular contemplated process, a plant treatment composition of the invention comprising glyphosate and a graminicide is applied to foliage of crop plants genetically transformed to tolerate glyphosate, and simultaneously to foliage of weeds or undesired plants growing in close proximity to such crop plants. Such crop plants must be tolerant also of the graminicide; this typically limits crops in which compositions of the invention are useful to broadleaf crops. Broadleaf crops genetically transformed to tolerate glyphosate include those whose seeds are sold by Monsanto or under license from Monsanto bearing the Roundup Ready® trademark. These include varieties of cotton, soybean, canola and sugar beet.

As glyphosate is generally very effective in controlling most grass weeds, the role of the graminicide in a glyphosate/graminicide composition is especially to control grasses that are themselves tolerant of glyphosate, principally descendants of genetically transformed crop plants of the grass family that have previously been grown on the land now being treated. For example, "volunteer" plants of corn arising from a previous crop of Roundup Ready® corn in a field now being used to grow Roundup Ready® soybeans, cannot be controlled by glyphosate alone, but are effectively controlled by a glyphosate/graminicide composition of the present invention.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon such factors as the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

EXAMPLES

The following examples are provided for illustrative purposes only and are not intended to limit the scope of the present invention. In these examples, percentage amounts refer to percent by weight unless otherwise noted. Abbreviations for glyphosate salts: IPA=isopropylammonium; MEA=monoethanolammonium.

Example 1

A microemulsion composition was prepared having the following ingredients:

| | |
|---|---|
| glyphosate IPA salt, 61.6% aqueous (MON 0139) | 68.57%[1] |
| ammonium chloride | 0.75% |
| 2N hydrochloric acid | 11.10% |
| Solvesso ™ Aromatic 150 | 8.20% |
| quizalofop-P-ethyl | 1.43% |
| polyoxyethylene (5) tallowamine | 3.11% |
| polyoxyethylene (2) cocoamine | 3.09% |
| polyoxyethylene (8) laurylether | 3.04% |
| water | 0.68% |

[1]42.24% glyphosate IPA salt; 31.33% glyphosate acid equivalent (a.e.)

Ammonium chloride was dissolved in 2N hydrochloric acid and the resulting solution was mixed with MON 0139 and additional water to form a first mixture. Quizalofop-P-ethyl was dissolved in Aromatic 150 to form a second mixture, which was then added with agitation to the first mixture. Finally the surfactants were added and the whole composition was stirred for 30 minutes.

The composition was a clear amber microemulsion that was physically stable at −10° C., room temperature (approximately 22° C.) and 50° C. The microemulsion exhibited good dispersion in water.

Example 2

A microemulsion composition was prepared having the following ingredients:

| | |
|---|---|
| glyphosate IPA salt, 61.6% aqueous (MON 0139) | 69.06%[1] |
| ammonium chloride | 1.75% |
| Solvesso ™ Aromatic 100 | 8.29% |
| quizalofop-P-ethyl | 1.46% |
| polyoxyethylene (5) tallowamine | 3.07% |
| polyoxyethylene (2) cocoamine | 2.97% |
| polyoxyethylene (6) laurylether | 2.24% |
| water | 11.15% |

[1]42.54% glyphosate IPA salt; 31.55% glyphosate acid equivalent (a.e.)

Ammonium chloride was dissolved in water and the resulting solution was mixed with MON 0139 to form a first mixture. Quizalofop-P-ethyl was dissolved in Aromatic 100 to form a second mixture, which was then added with agitation to the first mixture. Finally the surfactants were added and the whole composition was stirred for 30 minutes.

The composition was a clear amber microemulsion that was physically stable at −0° C., room temperature (approximately 22° C.) and 50° C. The microemulsion exhibited good dispersion in water.

Example 3

A microemulsion composition was prepared by the procedure of Example 2, using the following ingredients:

| | |
|---|---|
| glyphosate IPA salt, 61.6% aqueous (MON 0139) | 68.56%[1] |
| ammonium chloride | 1.53% |
| Solvesso ™ Aromatic 150 | 8.25% |
| quizalofop-P-ethyl | 1.46% |
| polyoxyethylene (5) tallowamine | 4.12% |
| polyoxyethylene (2) cocoamine | 4.07% |
| polyoxyethylene (6) laurylether | 2.07% |
| water | 9.94% |

[1]42.23% glyphosate IPA salt; 31.32% glyphosate acid equivalent (a.e.)

The composition was a clear amber microemulsion that was physically stable at −10° C., room temperature (approximately 22° C.) and 50° C. The microemulsion exhibited good dispersion in water.

Example 4

A microemulsion composition was prepared by the procedure of Example 2, using the following ingredients:

| | |
|---|---|
| glyphosate IPA salt, 61.6% aqueous (MON 0139) | 68.73%[1] |
| ammonium chloride | 1.75% |
| Solvesso ™ Aromatic 150 | 8.27% |
| quizalofop-P-ethyl | 1.46% |
| polyoxyethylene (5) tallowamine | 3.16% |
| polyoxyethylene (2) cocoamine | 2.95% |
| polyoxyethylene (8) laurylether | 2.57% |
| water | 11.12% |

[1]42.34% glyphosate IPA salt; 31.40% glyphosate acid equivalent (a.e.)

The composition was a clear amber microemulsion that was physically stable at −10° C., room temperature (approximately 22° C.) and 50° C. The microemulsion exhibited good dispersion in water.

Example 5

A microemulsion composition was prepared by the procedure of Example 2, using the following ingredients:

| | |
|---|---|
| glyphosate IPA salt, 61.6% aqueous (MON 0139) | 68.44%[1] |
| ammonium chloride | 1.52% |
| Solvesso ™ Aromatic 150 | 8.24% |
| quizalofop-P-ethyl | 1.45% |
| polyoxyethylene (5) tallowamine | 4.12% |
| polyoxyethylene (2) cocoamine | 4.25% |
| polyoxyethylene (6) laurylether | 2.06% |
| water | 9.92% |

[1]42.16% glyphosate IPA salt; 31.27% glyphosate acid equivalent (a.e.)

The composition was a clear amber microemulsion that was physically stable at −10° C., room temperature (approximately 22° C.) and 50° C. The microemulsion exhibited good dispersion in water.

Example 6

A microemulsion composition was prepared by the procedure of Example 2, using the following ingredients:

| | |
|---|---|
| glyphosate IPA salt, 61.6% aqueous (MON 0139) | 68.37%[1] |
| ammonium chloride | 1.52% |
| Solvesso ™ Aromatic 150 | 8.23% |
| quizalofop-P-ethyl | 1.45% |
| polyoxyethylene (5) tallowamine | 4.14% |
| polyoxyethylene (2) cocoamine | 4.07% |
| polyoxyethylene (6) laurylether | 2.32% |
| water | 9.90% |

[1]42.12% glyphosate IPA salt; 31.24% glyphosate acid equivalent (a.e.)

The composition was a clear amber microemulsion that was physically stable at −10° C., room temperature (approximately 22° C.) and 50° C. The microemulsion exhibited good dispersion in water.

Example 7

A microemulsion composition was prepared by the procedure of Example 2, using the following ingredients:

| | |
|---|---|
| glyphosate IPA salt, 61.6% aqueous (MON 0139) | 68.60%[1] |
| ammonium chloride | 1.22% |
| Solvesso ™ Aromatic 150 | 8.25% |
| quizalofop-P-ethyl | 1.46% |
| polyoxyethylene (5) tallowamine | 5.35% |
| polyoxyethylene (2) cocoamine | 5.11% |
| polyoxyethylene (6) laurylether | 2.00% |
| water | 8.02% |

[1]42.26% glyphosate IPA salt; 31.34% glyphosate acid equivalent (a.e.)

The composition was a clear amber microemulsion that was physically stable at −10° C., room temperature (approximately 22° C.) and 50° C. The microemulsion exhibited good dispersion in water.

Example 8

A microemulsion composition was prepared by the procedure of Example 2, using the following ingredients:

| | |
|---|---|
| glyphosate IPA salt, 61.6% aqueous (MON 0139) | 68.45%[1] |
| ammonium chloride | 1.52% |
| Solvesso ™ Aromatic 150 | 5.81% |
| quizalofop-P-ethyl | 1.45% |
| polyoxyethylene (5) tallowamine | 4.16% |
| polyoxyethylene (2) cocoamine | 4.04% |
| polyoxyethylene (6) laurylether | 2.08% |
| water | 12.48% |

[1]42.17% glyphosate IPA salt; 31.27% glyphosate acid equivalent (a.e.)

The composition was a clear amber microemulsion that was physically stable at −10° C., room temperature (approximately 22° C.) and 50° C. The microemulsion exhibited good dispersion in water.

Example 9

A microemulsion composition was prepared by the procedure of Example 2, using the following ingredients:

| | |
|---|---|
| glyphosate IPA salt, 61.6% aqueous (MON 0139) | 68.64%[1] |
| ammonium chloride | 1.74% |
| Solvesso ™ Aromatic 150 | 8.26% |
| quizalofop-P-ethyl | 1.43% |
| polyoxyethylene (5) tallowamine | 3.15% |
| polyoxyethylene (2) cocoamine | 3.24% |

-continued

| | |
|---|---|
| polyoxyethylene (6) laurylether | 2.08% |
| water | 11.43% |

[1] 42.28% glyphosate IPA salt; 31.36% glyphosate acid equivalent (a.e.)

The composition was a clear amber microemulsion that was physically stable at −10° C., room temperature (approximately 22° C.) and 50° C. The microemulsion exhibited good dispersion in water.

Example 10

A microemulsion composition was prepared by the procedure of Example 1, using the following ingredients:

| | |
|---|---|
| glyphosate IPA salt, 61.6% aqueous (MON 0139) | 68.58%[1] |
| ammonium chloride | 0.77% |
| hydrochloric acid, 37% aqueous | 1.88% |
| Solvesso ™ Aromatic 150 | 8.21% |
| quizalofop-P-ethyl | 1.43% |
| polyoxyethylene (5) tallowamine | 3.13% |
| polyoxyethylene (2) cocoamine | 3.09% |
| polyoxyethylene (6) laurylether | 2.02% |
| water | 10.87% |

[1] 42.25% glyphosate IPA salt; 31.33% glyphosate acid equivalent (a.e.)

The composition was a clear amber microemulsion that was physically stable at −10° C., room temperature (approximately 22° C.) and 50° C. The microemulsion exhibited good dispersion in water.

Example 11

A microemulsion composition was prepared by the procedure of Example 1, using the following ingredients:

| | |
|---|---|
| glyphosate IPA salt, 61.6% aqueous (MON 0139) | 68.52%[1] |
| ammonium chloride | 0.75% |
| 2N hydrochloric acid | 11.12% |
| Solvesso ™ Aromatic 150 | 8.22% |
| quizalofop-P-ethyl | 1.42% |
| polyoxyethylene (5) tallowamine | 3.12% |
| polyoxyethylene (2) cocoamine | 3.09% |
| polyoxyethylene (6) laurylether | 2.03% |
| water | 1.69% |

[1] 42.21% glyphosate IPA salt; 31.30% glyphosate acid equivalent (a.e.)

The composition was a clear amber microemulsion that was physically stable at −10° C., room temperature (approximately 22° C.) and 50° C. The microemulsion exhibited good dispersion in water.

Example 12

A microemulsion composition was prepared by the procedure of Example 1, using the following ingredients:

| | |
|---|---|
| glyphosate IPA salt, 61.6% aqueous (MON 0139) | 68.54%[1] |
| ammonium chloride | 0.75% |
| 2N hydrochloric acid | 11.12% |
| Solvesso ™ Aromatic 150 | 8.22% |
| quizalofop-P-ethyl | 1.42% |
| polyoxyethylene (5) tallowamine | 3.12% |
| polyoxyethylene (2) cocoamine | 3.09% |

-continued

| | |
|---|---|
| polyoxyethylene (8) laurylether | 2.61% |
| water | 1.09% |

[1] 42.22% glyphosate IPA salt; 31.31% glyphosate acid equivalent (a.e.)

The composition was a clear amber microemulsion that was physically stable at −10° C., room temperature (approximately 22° C.) and 50° C. The microemulsion exhibited good dispersion in water.

Example 13

A microemulsion composition was prepared having the following ingredients:

| | |
|---|---|
| glyphosate IPA salt, 62.2% aqueous (MON 0139) | 66.61%[1] |
| benzalkonium chloride | 8.21% |
| Solvesso ™ Aromatic 100 | 12.68% |
| quizalofop-P-ethyl | 1.38% |
| polyoxyethylene (5) tallowamine | 5.09% |
| polyoxyethylene (2) cocoamine | 6.00% |

[1] 41.43% glyphosate IPA salt; 30.73% glyphosate acid equivalent (a.e.)

Benzatkonium chloride was mixed with MON 0139, then, with agitation, polyoxyethylene (2) cocoamine and thereafter polyoxyethylene (5) tallowamine to form a first mixture. Quizalofop-P-ethyl was dissolved in Aromatic 100 to form a second mixture, which was then added with agitation to the first mixture. Finally the whole composition was stirred for 30 minutes.

The composition was a clear amber microemulsion that was physically stable at room temperature (approximately 22° C.) and 50° C. The microemulsion did not exhibit acceptable dispersion in water, instead forming an oil layer on the top of the water. (Note: the composition of this Example contained no nonionic surfactant as a dispersant.)

Example 14

A microemulsion composition was prepared by the procedure of Example 13, using the following ingredients:

| | |
|---|---|
| glyphosate IPA salt, 62.2% aqueous (MON 0139) | 72.94%[1] |
| benzalkonium chloride | 4.80% |
| Solvesso ™ Aromatic 100 | 8.76% |
| quizalofop-P-ethyl | 1.52% |
| polyoxyethylene (5) tallowamine | 5.98% |
| polyoxyethylene (2) cocoamine | 5.96% |

[1] 45.37% glyphosate IPA salt; 33.65% glyphosate acid equivalent (a.e.)

The composition was a clear amber microemulsion that was physically stable at room temperature (approximately 22° C.) and 50° C. The microemulsion did not exhibit acceptable dispersion in water. (Note: the composition of this Example contained no nonionic surfactant as a dispersant.)

Example 15

A microemulsion composition was prepared by the procedure of Example 13, using the following ingredients:

| | |
|---|---|
| glyphosate IPA salt, 62.2% aqueous (MON 0139) | 71.20%[1] |
| benzalkonium chloride | 6.41% |
| Solvesso ™ Aromatic 100 | 8.57% |
| quizalofop-P-ethyl | 1.48% |
| polyoxyethylene (5) tallowamine | 5.85% |
| polyoxyethylene (2) cocoamine | 6.46% |

[1] 44.29% glyphosate IPA salt; 32.85% glyphosate acid equivalent (a.e.)

The composition was a clear amber microemulsion that was physically stable at room temperature (approximately 22° C.) and 50° C. The microemulsion did not exhibit acceptable dispersion in water. (Note: the composition of this Example contained no nonionic surfactant as a dispersant.)

Example 16

A microemulsion composition was prepared having the following ingredients:

| | |
|---|---|
| glyphosate IPA salt, 62.2% aqueous (MON 0139) | 72.47%[1] |
| benzalkonium chloride | 4.39% |
| Solvesso ™ Aromatic 100 | 8.70% |
| quizalofop-P-ethyl | 1.54% |
| polyoxyethylene (5) tallowamine | 5.34% |
| polyoxyethylene (2) cocoamine | 5.39% |
| polyoxyethylene (6) laurylether | 2.17% |

[1] 45.08% glyphosate IPA salt; 33.43% glyphosate acid equivalent (a.e.)

Benzalkonium chloride was mixed with MON 0139, then, with agitation, polyoxyethylene (2) cocoamine, polyoxyethylene (5) tallowamine and polyoxyethylene (8) laurylether to form a first mixture. Quizalofop-P-ethyl was dissolved in Aromatic 100 to form a second mixture, which was then added with agitation to the first mixture. Finally the whole composition was stirred for 30 minutes.

The composition was a clear amber microemulsion that was physically stable at room temperature (approximately 22° C.) and 50° C. The microemulsion exhibited good dispersion in water.

Example 17

A microemulsion composition was prepared by the procedure of Example 16, using the following ingredients:

| | |
|---|---|
| glyphosate IPA salt, 62.2% aqueous (MON 0139) | 77.12%[1] |
| benzalkonium chloride | 3.34% |
| Solvesso ™ Aromatic 100 | 9.25% |
| quizalofop-P-ethyl | 1.60% |
| polyoxyethylene (5) tallowamine | 3.23% |
| polyoxyethylene (2) cocoamine | 3.20% |
| polyoxyethylene (6) laurylether | 2.23% |

[1] 47.97% glyphosate IPA salt; 35.58% glyphosate acid equivalent (a.e.)

The composition was a clear amber microemulsion that was physically stable at room temperature (approximately 22° C.) and 50° C. The microemulsion exhibited good dispersion in water.

Example 18

A microemulsion composition was prepared having the following ingredients:

| | |
|---|---|
| glyphosate IPA salt, 62.2% aqueous (MON 0139) | 67.62%[1] |
| isopropylamine | 7.10% |
| Solvesso ™ Aromatic 100 | 8.26% |
| quizalofop-P-ethyl | 1.43% |
| polyoxyethylene (2) tallowamine | 5.98% |
| polyoxyethylene (2) cocoamine | 9.59% |

[1] 42.06% glyphosate IPA salt; 31.19% glyphosate acid equivalent (a.e.)

Isopropylamine was added to MON 0139 to raise its pH, then, with agitation, the surfactants were added to form a first mixture. Quizalofop-P-ethyl was dissolved in Aromatic 100 to form a second mixture, which was then added with agitation to the first mixture. Finally the whole composition was stirred for 30 minutes. The composition had a pH of 7.4.

The composition was a clear amber microemulsion that was physically stable at room temperature (approximately 22° C.) and 50° C. The microemulsion did not exhibit acceptable dispersion in water. (Note: the composition of this Example contained no nonionic surfactant as a dispersant.)

Example 19

A microemulsion composition was prepared having the following ingredients:

| | |
|---|---|
| glyphosate IPA salt, 62.2% aqueous (MON 0139) | 70.70%[1] |
| benzalkonium chloride | 2.50% |
| Solvesso ™ Aromatic 100 | 8.51% |
| quizalofop-P-ethyl | 1.47% |
| polyoxyethylene (2) tallowamine | 5.49% |
| polyoxyethylene (2) cocoamine | 4.54% |
| polyoxyethylene (15) N-methyl cocoammonium chloride | 3.24% |
| polyoxyethylene (7) $C_{14-16}$ alkylether | 1.80% |
| DPGBE/DPG blend [2] | 1.72% |

[1] 43.98% glyphosate IPA salt; 32.62% glyphosate acid equivalent (a.e.)
[2] 55% DPGBE (dipropylene glycol butyl ether), 45% DPG (dipropylene glycol)

To MON 0139 were added the surfactants and the DPGBE/DPG blend to form first mixture. Quizalofop-P-ethyl was dissolved in Aromatic 100 to form a second mixture, which was then added with agitation to the first mixture. Finally the whole composition was stirred for 30 minutes.

The composition was a clear amber microemulsion that was physically stable at room temperature (approximately 22° C.) and 50° C. The microemulsion exhibited good dispersion in water.

Example 20

A microemulsion composition was prepared having the following ingredients:

| | |
|---|---|
| glyphosate IPA salt, 62.2% aqueous (MON 0139) | 77.69%[1] |
| ammonium chloride | 0.87% |
| 2N hydrochloric acid | 5.67% |
| Solvesso ™ Aromatic 150 | 6.60% |
| quizalofop-P-ethyl | 1.67% |
| polyoxyethylene (5) tallowamine | 3.51% |
| polyoxyethylene (2) cocoamine | 1.97% |
| polyoxyethylene (6) laurylether | 2.02% |

[1] 48.32% glyphosate IPA salt; 35.84% glyphosate acid equivalent (a.e.)

Ammonium chloride was dissolved in 2N hydrochloric acid and the resulting solution was mixed with MON 0139 to form a first mixture. Quizalofop-P-ethyl was dissolved in Aromatic 150 to form a second mixture, which was then added with agitation to the first mixture. Finally the surfactants were added and the whole composition was stirred for 30 minutes.

The composition was a clear amber microemulsion that was physically stable at room temperature (approximately 22° C.) and 50° C. The microemulsion exhibited good dispersion in water.

Example 21

A microemulsion composition was prepared by the procedure of Example 2, using the following ingredients:

| | |
|---|---|
| glyphosate MEA salt, 63.0% aqueous | 72.61%[1] |
| ammonium chloride | 1.88% |
| Solvesso ™ Aromatic 150 | 6.17% |
| quizalofop-P-ethyl | 1.54% |
| polyoxyethylene (15) cocoamine | 5.55% |
| polyoxyethylene (2) cocoamine | 4.76% |
| polyoxyethylene (6) laurylether | 2.12% |
| water | 5.36% |

[1] 45.74% glyphosate MEA salt; 33.64% glyphosate acid equivalent (a.e.)

The composition was a cloudy amber microemulsion that exhibited good dispersion in water.

Example 22

A microemulsion composition was prepared by the procedure of Example 1, using the following ingredients:

| | |
|---|---|
| glyphosate IPA salt, 62.2% aqueous (MON 0139) | 68.46%[1] |
| ammonium chloride | 0.88% |
| 2N hydrochloric acid | 11.53% |
| Solvesso ™ Aromatic 150 | 8.07% |
| quizalofop-P-ethyl | 1.68% |
| polyoxyethylene (5) tallowamine | 3.09% |
| polyoxyethylene (2) cocoamine | 3.07% |
| polyoxyethylene (8) laurylether | 2.63% |
| water | 0.55% |

[1] 42.58% glyphosate IPA salt; 31.58% glyphosate acid equivalent (a.e.)

The composition was a clear amber microemulsion that was physically stable at room temperature (approximately 22° C.) and 50° C. The microemulsion exhibited good dispersion in water.

Example 23

A microemulsion composition was prepared by the procedure of Example 20, using the following ingredients:

| | |
|---|---|
| glyphosate IPA salt, 62.2% aqueous (MON 0139) | 68.36%[1] |
| ammonium chloride | 0.98% |
| 2N hydrochloric acid | 10.00% |
| Solvesso ™ Aromatic 150 | 9.02% |
| quizalofop-P-ethyl | 2.49% |
| polyoxyethylene (5) tallowamine | 3.93% |
| polyoxyethylene (2) cocoamine | 2.56% |
| polyoxyethylene (8) laurylether | 2.61 |

[1] 42.52% glyphosate IPA salt; 31.54% glyphosate acid equivalent (a.e.)

The composition was a clear amber microemulsion that was physically stable at room temperature (approximately 22° C.) and 50° C. The microemulsion exhibited good dispersion in water.

Example 24

A microemulsion composition was prepared by the procedure of Example 1, using the following ingredients:

| | |
|---|---|
| glyphosate IPA salt, 62.2% aqueous (MON 0139) | 62.46%[1] |
| ammonium chloride | 1.21% |
| 2N hydrochloric acid | 15.15% |
| Solvesso ™ Aromatic 150 | 8.27% |
| quizalofop-P-ethyl | 2.28% |
| polyoxyethylene (5) tallowamine | 3.30% |
| polyoxyethylene (2) cocoamine | 3.00% |
| polyoxyethylene (8) laurylether | 2.64% |
| water | 1.64% |

[1] 38.85% glyphosate IPA salt; 28.81% glyphosate acid equivalent (a.e.)

The composition was a clear amber microemulsion that was physically stable at room temperature (approximately 22° C.) and 50° C. The microemulsion exhibited good dispersion in water.

Example 25

From each of the compositions of Examples 13–19, two aliquots were taken and stored in capped glass bottles. One aliquot of each composition was stored at room temperature (approximately 22° C.) and the other at 50° C. to accelerate any chemical degradation of the quizalofop-P-ethyl that might occur. After a period of storage, quizalofop-P-ethyl was assayed by HPLC. The compositions were prepared and put into storage on different dates, but all analyses were conducted on a single date, thus the period of storage varied among compositions. Quizalofop-P-ethyl assay in the room temperature samples was in some cases slightly higher than the calculated amount present. Thus an approximate measure of the degree of chemical degradation was taken by comparing, for each composition, the quizalofop-P-ethyl assay of the 50° C. sample with that of the room temperature sample. Results are shown in Table 1.

TABLE 1

| | | Quizalofop-P-ethyl assay (weight %) | | | |
|---|---|---|---|---|---|
| Composition | Days stored | calculated | found, 22° C. | found, 50° C. | % difference ("degradation") |
| Example 13 | 13 | 1.38 | 1.36 | 0.92 | 32.4 |
| Example 14 | 8 | 1.52 | 1.51 | 1.21 | 19.9 |
| Example 15 | 8 | 1.48 | 1.63 | 1.29 | 20.9 |
| Example 16 | 6 | 1.54 | 1.56 | 1.38 | 11.5 |
| Example 17 | 6 | 1.60 | 1.69 | 1.63 | 3.6 |
| Example 18 | 6 | 1.43 | 1.52 | 0.88 | 42.1 |
| Example 19 | 5 | 1.47 | 1.61 | 1.39 | 13.7 |

Only the composition of Example 17 exhibited an acceptably low rate of quizalofop-P-ethyl degradation in this study. It will be noted that this composition has less than about 10% (in fact 6.43%) by weight of an emulsifying system formed of tertiary amine surfactants, less than about 6% (in fact 3.34%) by weight of benzalkonium chloride and less than about 5% (in fact 2.23%) by weight of a dispersing system formed of a polyoxyethylene alkylether surfactant. The total amount of all surfactants present in the composition of Example 17 is 12.00% by weight.

Example 26

From each of the compositions of Examples 1–12, three aliquots were taken and stored in capped glass bottles. One aliquot of each composition was stored at room temperature (approximately 22° C.), one at 40° C. and one at 50° C. to accelerate any chemical degradation of the quizalofop-P-ethyl that might occur. After various periods of storage, quizalofop-P-ethyl was assayed by HPLC. Assays were compared with those from freshly prepared samples of each composition to determine the degree of chemical degradation, which was calculated as percentage assay loss. Results are shown in Table 2. Blank cells in Table 2 indicate that no data are available.

TALBE 2

| Composition | Storage temperature | % quizalofop-P-ethyl assay loss | | | | |
|---|---|---|---|---|---|---|
| | | 14 d | 28 d | 42 d | 56 d | 84 d |
| Example 1 | 22° C. | 0.0 | 0.7 | 0.7 | 1.4 | 1.4 |
| | 40° C. | 1.4 | 1.5 | 5.7 | 10.1 | 10.6 |
| | 50° C. | 3.5 | 2.9 | 9.0 | 20.9 | 23.2 |
| Example 2 | 22° C. | 1.3 | 1.9 | 1.9 | 0.0 | 0.6 |
| | 40° C. | 1.9 | 4.5 | 5.8 | 3.4 | 10.3 |
| | 50° C. | 4.5 | 9.7 | 13.5 | 14.2 | 28.4 |
| Example 3 | 22° C. | 0.6 | 0.0 | | 0.7 | 4.3 |
| | 40° C. | 2.7 | 2.0 | | 12.7 | 17.3 |
| | 50° C. | 6.1 | 8.1 | | 32.0 | 42.6 |
| Example 4 | 22° C. | 0.6 | 1.9 | | 1.3 | 2.5 |
| | 40° C. | 2.5 | 5.3 | | 7.2 | 11.6 |
| | 50° C. | 4.3 | 11.2 | | 21.1 | 28.2 |
| Example 5 | 22° C. | 0.0 | 0.0 | | | 4.3 |
| | 40° C. | 3.1 | 5.3 | | | 17.9 |
| | 50° C. | 6.2 | 18.9 | | | 43.2 |
| Example 6 | 22° C. | 0.0 | 0.0 | | 0.0 | 5.5 |
| | 40° C. | 0.0 | 2.1 | | 9.4 | 18.9 |
| | 50° C. | 1.9 | 8.9 | | 30.9 | 44.5 |
| Example 7 | 22° C. | 1.3 | 0.0 | | | 4.5 |
| | 40° C. | 6.4 | 8.3 | | | 24.8 |
| | 50° C. | 14.7 | 24.3 | | | 60.5 |
| Example 8 | 22° C. | 1.3 | 1.9 | | | |
| | 40° C. | 3.9 | 5.8 | | | |
| | 50° C. | 9.7 | 15.6 | | | |
| Example 9 | 22° C. | 1.8 | 1.3 | 1.9 | 2.7 | |
| | 40° C. | 3.6 | 5.2 | 8.0 | 11.6 | |
| | 50° C. | 6.1 | 11.4 | 16.0 | 23.0 | |
| Example 10 | 22° C. | 2.5 | 0.6 | 0.7 | 1.4 | |
| | 40° C. | 3.2 | 3.3 | 4.9 | 7.0 | |
| | 50° C. | 4.4 | 8.0 | 9.8 | 13.3 | |
| Example 11 | 22° C. | 0.0 | 0.7 | 1.4 | 0.0 | 0.7 |
| | 40° C. | 0.0 | 2.8 | 4.3 | 5.6 | 8.9 |
| | 50° C. | 1.4 | 5.6 | 10.0 | 15.4 | 26.9 |
| Example 12 | 22° C. | 0.0 | | | 0.7 | |
| | 40° C. | 2.2 | | | 6.3 | |
| | 50° C. | 3.6 | | | 17.5 | |

The compositions of Examples 1–12 can be seen from the data in Table 2 to fall into three groups with respect to the degree of chemical degradation of quizalofop-P-ethyl exhibited. When stored at 40° C. for 84 days, the degree of degradation was less than 15% in the first group, 15–20% in the second group and greater than 20% in the third group. When stored at 50° C. for 84 days, the degree of degradation was less than 30% in the first group, 30–50% in the second group and greater than 50% in the third group. Where no data for the 84 day period are available, a composition can be placed in one of these three groups by a reasonable extrapolation of data for a shorter period.

The first group, showing the least chemical degradation of quizalofop-P-ethyl, comprises the compositions of Examples 1, 2, 4, 9, 10, 11 and 12. All of these are compositions of a preferred embodiment of the present invention having approximately 6% by weight of an emulsifying system formed of tertiary amine surfactants.

The second group, showing a rather greater degree of chemical degradation of quizalofop-P-ethyl, comprises the compositions of Examples 3, 5, 6 and 8. All of these are compositions of a less preferred embodiment of the present invention having approximately 8% by weight of an emulsifying system formed of tertiary amine surfactants.

The third group, showing a still greater degree of chemical degradation of quizalofop-P-ethyl, comprises the composition of Example 7. This composition has over 10% by weight of an emulsifying system formed of tertiary amine surfactants.

Example 27

The compositions of Examples 1, 11, 12 and 20–24 were evaluated for crop safety in a greenhouse test by foliar application to Roundup Ready® soybeans, Roundup Ready® canola and Roundup Ready® sugar beet, and for herbicidal effectiveness on Roundup Ready® corn (maize), Roundup Ready® rice and Roundup Ready® wheat. For comparative purposes, the following commercial standard formulations were included in the test:

Roundup® Ultra herbicide of Monsanto, an aqueous solution concentrate formulation containing glyphosate IPA salt together with a surfactant.

Assure® II herbicide of Du Pont, an emulsifiable concentrate formulation containing quizalofop-P-ethyl.

The following procedure was used for the greenhouse test. Seeds of the plant species indicated were planted in 85 mm square pots in a soil mix which had previously been steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels. Relative humidity was maintained at about 50% for the duration of the test.

Pots were assigned to different treatments in a fully randomized experimental design with 3 replications. A set of pots was left untreated as a reference against which effects of the treatments were later evaluated.

Application of glyphosate compositions to foliage was made by spraying with a track sprayer fitted with a TeeJet™ 9501E nozzle calibrated to deliver a spray volume of 93 liters per hectare (l/ha) at a pressure of 166 kilopascals (kPa). Application was made when the plants were about 2 weeks old. After treatment, pots were returned to the greenhouse until ready for evaluation.

Treatments were made using dilute aqueous compositions, prepared by dilution with water of preformulated concentrate compositions. Comparisons were made at equal glyphosate acid equivalent rates. The required degree of dilution for a glyphosate concentrate composition to make a plant treatment composition was calculated from the equation $$A = RS/VC$$

where A is the volume in milliliters (ml) of the glyphosate composition to be added to the plant treatment composition being prepared, R is the desired glyphosate rate in grams of acid equivalent per hectare (g a.e./ha), S is the total volume in milliliters (ml) of plant treatment composition being prepared, V is the application rate in liters per hectare (l/ha) of plant treatment composition, conventionally referred to as "spray volume", and C is the concentration of glyphosate in grams of acid equivalent per liter (g a.e./l) in the glyphosate composition.

Assure® was applied together with a commercial nonionic surfactant adjuvant at 0.25% by volume of the plant treatment composition, as recommended on the Assure® II label. Where Assure® II was applied in tank mixture with Roundups Ultra, no nonionic surfactant was added.

For evaltion of crop safety and herbicidal effectiveness, all plants in the test were examined by a single practiced technician, who recorded percent injury or inhibition, a visual measurement of the phytotoxicity of each treatment by comparison with untreated plants. Inhibition or injury of 0% indicates no effect, and inhibition of 100% indicates that all of the plants are completely dead. Crop injury levels of 15% or less are in most cases considered acceptable for normal use, although it is generally desired to have injury levels of 5% or less. Inhibition of 85% or more is in most cases considered acceptable for normal herbicidal use on weeds to be controlled.

Results of the test of Example 27 are given in Table 3. Blank cells in Table 3 indicate that no are available.

TABLE 3

| | Rate (g/ha) | | % injury | | | % inhibition | | |
|---|---|---|---|---|---|---|---|---|
| Composition | gly a.e.[1] | quiz[2] | soy[3] | canola[4] | beet[5] | corn[6] | rice[7] | wheat[8] |
| Roundup | 420 | 0 | 2 | 0 | | 0 | | |
| Ultra | 627 | 0 | 4 | 9[9] | 0 | 0 | 0 | 0 |
| | 840 | 0 | 4 | 3 | 0 | 0 | 0 | 0 |
| | 1680 | 0 | 4 | | 5 | 0 | 13 | 0 |
| Assure II | 0 | 19 | 0 | 0 | | 100 | 97 | 100 |
| | 0 | 29 | 2 | 0 | 0 | 100 | 100 | 100 |
| | 0 | 38 | 3 | 0 | 0 | 100 | 97 | 100 |
| | 0 | 76 | 10 | | 0 | 100 | 100 | 100 |
| tank mix | 420 | 19 | 2 | 1 | | 100 | 100 | 100 |
| Roundup | 627 | 29 | 5 | 2 | 0 | 100 | 100 | 100 |
| Ultra + | 840 | 38 | 3 | 2 | 0 | 100 | 100 | 100 |
| Assure II | 1680 | 76 | 8 | | 1 | 100 | 100 | 100 |
| Ex. 1 | 420 | 19 | 0 | 0 | | 100 | | |
| | 627 | 29 | 0 | 8 | 0 | 100 | 100 | 100 |
| | 840 | 38 | 2 | 10 | 0 | 100 | 100 | 100 |
| | 1680 | 76 | 2 | | 1 | 100 | 100 | 100 |
| Ex. 11 | 420 | 19 | 0 | 0 | | 100 | | |
| | 627 | 29 | 1 | 2 | 0 | 100 | 100 | 100 |
| | 840 | 38 | 1 | 7 | 1 | 100 | 100 | 100 |
| | 1680 | 76 | 5 | | 2 | 100 | 100 | 100 |
| Ex. 12 | 420 | 19 | 1 | 0 | | 100 | | |
| | 627 | 29 | 0 | 2 | 0 | 100 | 100 | 100 |
| | 840 | 38 | 0 | 2 | 2 | 100 | 100 | 100 |
| | 1680 | 76 | 2 | | 1 | 100 | 100 | 100 |
| Ex. 20 | 627 | 29 | | 2 | 0 | | | |
| | 840 | 38 | | 5 | 0 | | | |
| | 1680 | 76 | | 12 | 0 | | | |
| Ex. 21 | 627 | 29 | | 0 | 0 | | | |
| | 840 | 38 | | 3 | 0 | | | |
| | 1680 | 76 | | 15 | 0 | | | |
| Ex. 22 | 420 | 23 | 2 | 0 | | 100 | 100 | 100 |
| | 627 | 34 | 3 | 1 | 0 | 100 | 90 | 100 |
| | 840 | 45 | 5 | 4 | 0 | 100 | 97 | 100 |
| | 1680 | 90 | 11 | | 6 | 100 | 93 | 100 |
| Ex. 23 | 420 | 34 | 5 | 0 | | 100 | 100 | |
| | 627 | 50 | 12 | 2 | 0 | 100 | 100 | 100 |
| | 840 | 67 | 13 | 1 | 0 | 100 | 100 | 100 |
| | 1680 | 134 | 15 | | 8 | 100 | 100 | 100 |
| Ex. 24 | 420 | 34 | 3 | 0 | | 100 | 100 | |
| | 627 | 50 | 5 | 3 | 0 | 100 | 100 | 100 |
| | 840 | 67 | 6 | 0 | 2 | 100 | 100 | 100 |
| | 1680 | 134 | 7 | | 0 | 100 | 100 | 100 |

[1] glyphosate acid equivalent
[2] quizalofop-P-ethyl
[3] Roundup Ready ® soybean, evaluated 7 days after treatment
[4] Roundup Ready ® canola, evaluated 6 days after treatment
[5] Roundup Ready ® sugar beet, evaluated 6 days after treatment
[6] Roundup Ready ® corn (maize), evaluated 13 days after treatment
[7] Roundup Ready ® rice, evaluated 12 days after treatment
[8] Roundup Ready ® wheat, evaluated 23 days after treatment
[9] this data point probably represents an error in treatment and should be disregarded

Example 28

A microemulsion composition was prepared by the procedure of Example 1 (except glufosinate IPA salt was substituted for glyphosate IPA salt), using the following ingredients:

| | |
|---|---|
| glufosinate IPA salt, 50% aqueous | 67.83%* |
| ammonium chloride | 0.71% |
| 2N hydrochloric acid | 10.89% |
| Solvesso ™ Aromatic 150 | 8.16% |
| quizalofop-P-ethyl | 1.41% |
| polyoxyethylene (5) tallowamine | 3.07% |
| polyoxyethylene (2) cocoamine | 3.10% |
| polyoxyethylene (6) laurylether | 0.73% |
| water | 4.06% |

*34.05% glufosinate IPA salt; 31.04% glufosinate acid equivalent (a.e.)

The composition was a clear amber microemulsion that was physically stable at −10° C., room temperature (approximately 22° C.) and 50° C. The microemulsion exhibited good dispersion in water.

Example 28C

For comparative purposes, a "control" microemulsion composition (similar to the composition of Example 28, except that no ammonium chloride, hydrochloric acid or water was employed) was prepared having the following ingredients:

| | |
|---|---|
| glufosinate IPA salt, 50% aqueous | 67.24%* |
| ammonium chloride | 0.00% |
| 2N hydrochloric acid | 0.00% |
| Solvesso ™ Aromatic 150 | 3.03% |
| quizalofop-P-ethyl | 1.40% |
| polyoxyethylene (5) tallowamine | 13.59% |
| polyoxyethylene (2) cocoamine | 13.94% |
| polyoxyethylene (6) laurylether | 0.77% |
| water | 0.00% |

*34.05% glufosinate IPA salt; 31.04% glufosinate acid equivalent (a.e.)

The composition was a clear amber microemulsion that was physically stable at −10° C., room temperature (approximately 22° C.) and 50° C. The microemulsion exhibited good dispersion in water.

Example 29

From each of the compositions of Examples 28 and 28 C, four aliquots were taken and stored in capped glass bottles. One aliquot of each composition was stored at room temperature (approximately 22° C.), one at 40° C., one at 50° C., and one at 60° C. After 14 days of storage, quizalofop-P-ethyl was assayed by HPLC. Assays were compared with the freshly prepared samples of each composition to determine the degree of chemical degradation, which was calculated as percent assay loss. The results are shown Table 4.

TABLE 4

| Composition | Storage Temperature | % quizalofop-P-ethyl loss after 14 days storage |
|---|---|---|
| Example 28 | 22° C. | 0 |
| | 40° C. | 1.4 |
| | 50° C. | 3.5 |
| | 60° C. | 10 |

TABLE 4-continued

| Composition | Storage Temperature | % quizalofop-P-ethyl loss after 14 days storage |
|---|---|---|
| Example 28C | 22° C. | 0 |
| | 40° C. | 37 |
| | 50° C. | 60 |
| | 60° C. | 77 |

As seen from the data in Table 4, the % quizalofop loss after 14 days is greatly reduced when a preferred embodiment of the present invention is employed. It can also be seen that the relative loss of assay for quizalofop/glufosinate mixtures is similar to that for quizalofop/glyphosate mixtures (See Table 2, Example 1).

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A liquid concentrate herbicidal microemulsion composition having a continuous aqueous phase and a discontinuous oil pheause, comprising (i) water in said aqueous phase;

(ii) a water-soluble herbicide dissolved in said water in an amount which is biologically effective when the compositioin is diluted in a suitable volunme of water and applied to foliage of a susceptible plant;

(iii) an oil-soluble graminicide in said oil phase having the chemical formula (I)

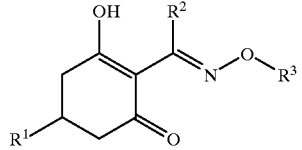

(I)

where $R^1$ is a butyryl, (2-ethylthio)propyl or 2,4,6-trimethylphenyl group or a group

wherein X is O or S; $R^2$ is a $C_{1-4}$ alkyl group; and $R^3$ is an ethyl, allyl or 3- haloallyl group; or the chemical formula (II)

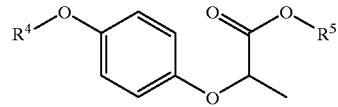

(II)

where $R^4$ is a group

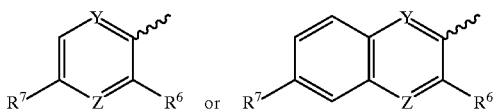

wherein $R^6$ and $R^7$ are independently selected from hydrogen, halogen, methyl, trifluoromethyl and cyano groups, and Y and Z are independently selected from CH and N, at least one of Y and Z being N; and $R^5$ is a hydrogen, $C_{1-4}$ alkyl, allyl, propargyl, tetrahydrofurfuryl, 2-ethoxyethyl or 2-isopropylideneaminooxyethyl group; said graminicide being present in a weight ratio to said water-soluble herbicide of about 1:50 to about 1:1;

(iv) a substantially water-immiscible organic solvent in said oil phase selected such that said graminicide has an organic solvent/water partition coefficient, expressed as a logarithm, of about 4 or greater, said organic solvent being present in a weight ratio to said graminicide of about 3:1 to about 30:1;

(v) an emulsifying system comprising one or more surfactants each having a tertiary amine functional group, in an amount not exceeding about 10% by weight of the composition but sufficient to provide acceptable physical stability of the microemulsion;

(vi) a stabilizing amount of one or more water-soluble chlorides selected from hydrochloric acid, alkali metal chlorides, ammonium chloride, low molecular weight organic ammonium chlorides and quaternary ammonium chloride surfactants; and (vii) a dispersing system comprising one or more nonionic surfactants, in a total amount not exceeding about 5% by weight but sufficient to provide acceptable dispersion of the microemulsion upon dilution thereof in a suitable volume of water for application to plants and not sufficient to destabilize the microemulsion.

2. A composition of claim 1 that contains about 5% to about 50% by weight in total of the water-soluble herbicide and the graminicide.

3. A composition of claim 1 that contains about 20% to about 50% by weight in total of the water-soluble herbicide and the graminicide.

4. A composition of claim 1 wherein the water-soluble herbicide is selected from acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

5. A composition of claim 1 wherein the water-soluble herbicide is a salt of glyphosate.

6. A composition of claim 5 wherein the salt of glyphosate is selected from the alkali metal, ammonium, $C_{1-6}$ alkylammonium, $C_{1-6}$ alkanolammonium and $C_{1-6}$ alkylsulfonium salts.

7. A composition of claim 1 wherein the graminicide is selected from butroxydim, clethodim, cycloxydim, sethoxydim, tepraloxydim, haloxyfop, propaquizafop and the $C_{4-1}$ alkyl and propargyl esters of clodinafop, cyhalofop, diclofop, fluazifop, fluazifop-P, quizalofop and quizalofop-P.

8. A composition of claim 1 wherein the water-soluble herbicide is a salt of glyphosate and the graminicide is quizalofop-P-ethyl.

9. A composition of claim 1 wherein the organic solvent is selected such that said graminicide has an organic solvent/water partition coefficient, expressed as a logarithm, of about 5 or greater.

10. A composition of claim 1 wherein the organic solvent is an aromatic solvent.

11. A composition of claim 1 wherein the organic solvent is present in a weight ratio to said graminicide of about 4:1 to about 10:1.

12. A composition of claim 1 wherein the amount of all surfactants in the composition is less than about 12% by weight.

13. A composition of claim 1 wherein the emulsifying system comprises one or more surfactants selected from polyoxyethylene (2-20) tertiary alkylamines and polyoxyethylene (2-20) tertiary alkyletheramines.

14. A composition of claim 13 wherein said alkylamines and alkyletheramines have alkyl chains having about 12 to about 18 carbon atoms.

15. A composition of claim 13 wherein the amount of said alkylamine and/or alkyletheramine surfactants is about 3% to about 10% by weight.

16. A composition of claim 13 wherein the amount of said alkylamine and/or alkyletheramine surfactants is about 3% to about 6% by weight.

17. A composition of claim 1 wherein a water-soluble quaternary ammonium chloride surfactant is present at about 1% to about 6% by weight.

18. A composition of claim 17 wherein said quaternary ammonium chloride surfactant is benzalkonium chloride.

19. A composition of claim 1 wherein one or more chlorides selected from low molecular weight organic ammonium chlorides, ammonium chloride, alkali metal chlorides and hydrochloric acid are present in an amount providing about 0.5% to about 2.5% chloride ion by weight.

20. A composition of claim 19 wherein the chlorides are one or both of ammonium chloride and hydrochloric acid.

21. A composition of claim 1 wherein the dispersing system comprises one or more nonionic surfactants selected from polyoxyethylene (2-20) alkylethers and alkylphenylethers.

22. A composition of claim 21 wherein the amount of said nonionic surfactants is about 1% to about 3% by weight.

23. A composition of claim 1 wherein the aqueous phase has a pH in a range that is minimally conducive to chemical degradation of the graminicide.

24. A process for killing or controlling unwanted plants, comprising diluting a composition of claim 1 in a suitable volume of water to form a plant treatment composition, and applying the plant treatment composition to foliage of the unwanted plants.

25. A process of claim 24 wherein the unwanted plants comprise descendants of crop plants of the grass family genetically transformed to tolerate the water-soluble herbicide present in the composition, and said unwanted plants are growing in a broadleaf crop genetically transformed to tolerate said water-soluble herbicide.

26. A process of claim 25 wherein the water-soluble herbicide present in the composition is glyphosate, said descendants of crop plants of the grass family are selected from glyphosate-tolerant corn, rice and wheat and said broadleaf crop is selected from glyphosate-tolerant cotton, soybeans, rapeseed, canola and sugar beet.

* * * * *

UNITED STATES PATENT AND TRADEMARK OFFICE
CERTIFICATE OF CORRECTION

PATENT NO. : 6,369,001 B1
DATED : April 9, 2002
INVENTOR(S) : Ganiyu A. Jimoh

It is certified that error appears in the above-identified patent and that said Letters Patent is hereby corrected as shown below:

Column 30,
Line 29, "phease" should read -- phase --.
Lines 33-34, "compositioin" should read -- composition --.
Line 34, "volunme" should read -- volume --.

Column 31,
Line 66, "$C_{4-1}$" should read -- $C_{1-4}$ --.

Signed and Sealed this

Tenth Day of February, 2004

JON W. DUDAS
*Acting Director of the United States Patent and Trademark Office*